United States Patent
Imbert et al.

(10) Patent No.: US 8,365,602 B2
(45) Date of Patent: Feb. 5, 2013

(54) WELD SEAM TRACKING SYSTEM USING PHASED ARRAY ULTRASONIC DEVICES

(75) Inventors: Christophe Claude Imbert, St Augustin de Desmaures (CA); Jinchi Zhang, Quebec (CA)

(73) Assignee: Olympus NDT, Inc., Waltham, MA (US)

( * ) Notice: Subject to any disclaimer, the term of this patent is extended or adjusted under 35 U.S.C. 154(b) by 684 days.

(21) Appl. No.: 12/576,610

(22) Filed: Oct. 9, 2009

(65) Prior Publication Data

US 2011/0083512 A1  Apr. 14, 2011

(51) Int. Cl.
*G01N 29/26* (2006.01)
(52) U.S. Cl. .......................... 73/622; 220/104
(58) Field of Classification Search ............... 73/622, 73/634; 228/104, 56.5
See application file for complete search history.

(56) References Cited

U.S. PATENT DOCUMENTS

| | | | | |
|---|---|---|---|---|
| 5,583,292 A | * | 12/1996 | Karbach et al. | 73/638 |
| 5,677,490 A | * | 10/1997 | Gunther et al. | 73/622 |
| 7,094,989 B2 | * | 8/2006 | McJunkin et al. | 73/624 |
| 2009/0132181 A1 | * | 5/2009 | Girndt | 702/39 |

* cited by examiner

*Primary Examiner* — John Chapman, Jr.
(74) *Attorney, Agent, or Firm* — Ostrolenk Faber LLP

(57) ABSTRACT

A weld seam tracking device for tracking weld seams on pipes or the like uses NDT/NDI sensor(s) in conjunction with an NDT/NDI operation, such as an ultrasonic phased array (PA) inspection. Processing of the weld seam tracking data is integrated or combined with the existing data processing element of the existing NDT/NDI inspection devices. Wide scanning areas of phased array probes allow weld seam tracking and inspection to be performed using a single set of probe and data processing elements to achieve both fault scanning and seam tracking with a single run of the PA scan.

17 Claims, 10 Drawing Sheets

WELD SEAM TRACKING SYSTEM USING PHASED ARRAY ULTRASONIC DEVICES

FIELD OF THE INVENTION

The present invention relates to non-destructive testing and inspection systems (NDT/NDI) and more particularly to an automatic weld seam tracking system using phased array (PA) devices in conjunction with NDT/NDI inspection operations.

BACKGROUND OF THE INVENTION

Welding is a long practiced process for joining separate metal objects together for the purpose of building support structures and producing pipes, vessles and other products. There are many types of welding techniques including gas welding, electric arc welding and electric resistance welding (ERW). A common characteristic of welded objects is the difference in thickness between the welded and non-welded regions.

Inspection of weld integrity has long been recognized as crucially important because it enables the detection of cracking, porosity, incomplete penetration, inclusions, lack of sidewall fusion, and other defects that can compromise weld strength. Many existing NDT/NDI products are available for weld inspection, such as ultrasonic and eddy current instruments and probes.

For some weld inspection applications, one of the challenges lies in how to efficiently and/or automatically track the position of the welds and therefore guide the inspection probes that are placed in immediate proximity of the welds. For example, for electronic resistance welding (ERW) production, pipes are formed by feeding rectangular metal sheets into the welder to have their opposite sides welded together. Then the weld seam is trimmed on both outer and inner surfaces before leaving the welding and weld verification system.

In one of the existing practices, the weld seam integrity is inspected while being transported through the welding and weld inspection system by an ultrasonic phased array (PA) system. The weld seam position on long pipes has a tendency to drift circumferentially while in transport requiring an operator to visually monitor the weld seam position and adjust the pipe or the PA probe position to remain centered over the weld seam. It should be noted that it is not uncommon for the weld seam location to drift only a few degrees for every 50 meter of pipe's axial movement.

One of the drawbacks of the manual tracking method described above is that it prevents the full automation of the welding and weld inspection system because the operator must be present to monitor and adjust the weld seam location as required.

To overcome the problem of weld seam tracking, some existing efforts came to the applicants' knowledge including a solution provided by Metavision of the United Kingdom. The Metavision device uses laser tracking technology to guide NDI inspection. A limitation presented by this method is that it requires a visible marked line along the pipe to guide the PA probe to follow the weld seam. Painting a visible line (called also the pilot line) at a given distance from the weld seam presents quite some degree of difficulties under industrial operation conditions. In order to be precise, the pilot line has to be painted near the welding process location where the temperature is hot, consequently causing the marked line to lack paint or be partially masked. The laser tracking device, an optical device, is used to monitor the contrast between the dark surface on the pipe and the white line to establish proper position. If the contrast is poor, the device could lose the weld position.

Additional disadvantages of the Metavision device also include the use of a laser sensor and the need for two separate sets of sensors and associated hardware/software for weld seam tracking and inspection tasks, which leads to undesirable higher system investment.

Another solution is described in US patent application (publication number 2009/0132181 A1) by Girndt. The Girndt patent application addresses the weld seam tracking problem by employing an ultrasonic sensor to track the weld seam using two sets of sensors—one for tracking and the other for inspecting the weld seam, which presents increased material and operational costs.

Girndt also fails to mention the usage of phased array ultrasonic system, which prevents obtaining the capability to cover a wider stripe of scanning area along weld seam and its vicinity. Furthermore, Girndt presents the limitation of requiring the scanning of the whole external pipe surface to obtain the weld seam position, which is extremely inefficient compared to scanning only the weld seam and the bordering region.

SUMMARY OF THE INVENTION

The invention disclosed herein aims to solve the problems related to weld seam tracking for positioning NDT/NDI devices to perform weld seam inspections, while avoiding the existing weld seam tracking techniques having the aforementioned drawbacks, such as inefficiency and high cost of manual tracking or using extra sensor/tracking devices external to the NDT/NDI inspection devices.

It should be noted that sensor, probe and transducer are herein used in the present disclosure interchangeably.

Accordingly, it is a general object of the present disclosure to provide a weld seam tracking device that directly uses NDT/NDI sensor(s) in conjunction with an NDT/NDI operation. Processing of the weld seam tracking algorithm can be easily integrated to or combined with the existing data processing element of existing NDT/NDI inspection devices.

It is further an object of the present disclosure to make use of an inspection sensor of a phased array (PA) system and make use of conventional PA processed data, such as C-scan, and extract thickness variation information from the C-scan to identify weld seam location.

It is further an object of the present disclosure to make use of the advantages of PA probes which provide a wider scan area than that of single or dual element probes, so that the scan area can cover the whole width of a weld seam and its vicinity. This is significant because it allows weld seam tracking and inspection to be done smoothly in one move along the direction of weld seam. It inherently eliminates the need to move the sensor across a large or the whole surface of the test object to locate the weld seam.

It is further an object of the present disclosure to perform weld seam tracking in conjunction of weld inspection, eliminating the need for any extra sensors, such as laser or infra-red sensor, and the need of any extra data processing capacity related to the extra sensors. Inherently, the novel approach as disclosed reduces material and operational cost, and increases operational efficiency.

It is yet further another object of the present disclosure to present real-time weld seam location images in a PA C-scan to the operators, which allows a semi-automatic tracking or occasionally optional manual tracking of weld seams during weld inspection process.

It is further an object of the present disclosure to provide a software or firmware program to enable an existing PA inspection system to perform weld seam tracking while performing weld inspections.

DETAILED DESCRIPTION OF THE INVENTION

Figure 1:
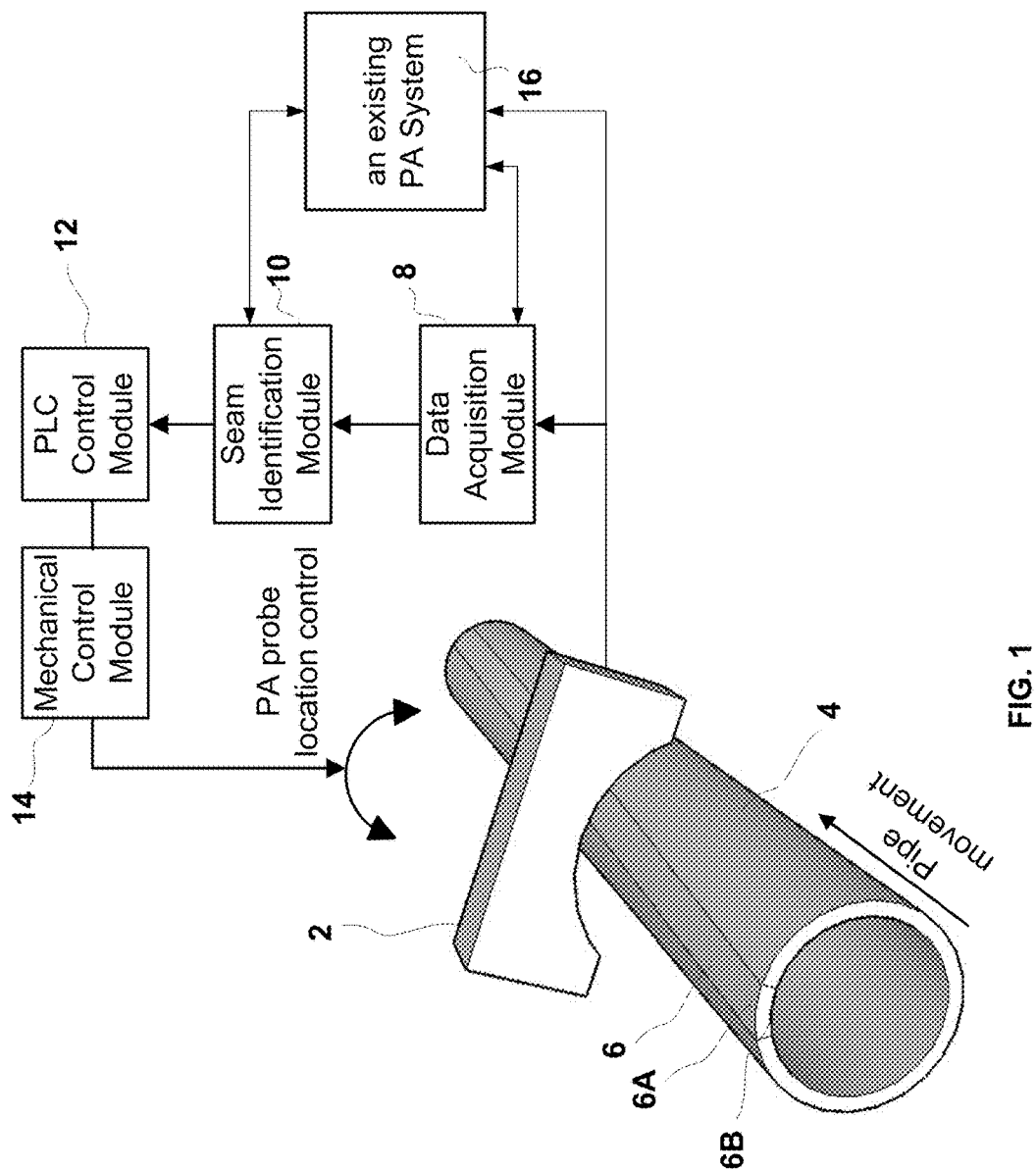
FIG. 1 is a schematic diagram showing the presently disclosed weld seam tracking device using a phased array system.

Referring to FIG. 1, the presently disclosed weld seam tracking device using a phased array system is comprised of a PA probe 2; a data acquisition module 8, a weld seam identification module 10 and a process logic control (PLC) control module 12 and a mechanical control module 14.

Using a conventional welding system production procedure as an example, pipe 4 is formed by being passed through a welding machine (not shown) to weld the two opposite edges of a bent rectangular metal sheet in order to form weld seam 6. Then, outer connecting surface 6A and inner connecting surface 6B of weld seam 6 are trimmed by the welding machine as the pipe moves away from the welding machine toward PA probe 2, creating a zone of thickness variation. During the process, the weld seam 6 on each pipe 4 may wander circumferentially on the transport mechanism (not shown) while the pipe is leaving the welding machine.

The presently disclosed weld seam and/or trimmed zone tracking device preferably uses a conventional phased-array inspection system 16 in order to perform weld tracking and inspection with the same equipment. For example, in the conventional PA system inspecting weld seams, PA probe 2 is cylindrically curved at its inspection surface and acoustically coupled via water (not shown) to pipe 4. Probe 2 scans circumferentially the weld seam and its vicinity while pipe 4 is moving axially passing probe 2. Probe 2 typically detects the thickness of weld seam 6 confined by the outer connecting surface 6A and inner connecting surface 6B, and detects also the thickness in the vicinity of seam 6.

Continuing with FIG. 1, the focusing, firing and positioning of probe 2 to follow the track of seam 6 are controlled collectively by data acquisition module 8, weld seam identification module 10 and control modules 12 and 14. It is important to note that the conventional PA inspection process may be conducted in parallel simultaneously, or interspersed, with the weld seam tracking process of the present invention. For simplicity of explanation, the present disclosure focuses primarily on the weld seam tracking process.

Acquisition module 8 preferably receives the thickness measurements of weld seam 6 and its vicinity using the C-scan method both for conventional PA inspection and the presently disclosed weld seam tracking purposes. The thickness information provided for the C-scan is fed by PA system 16 through acquisition module 8 to weld seam identification module 10. The differences and/or pattern of the weld seam thickness compared to the non-welded vicinity of pipe 4 are analyzed by seam identification module 10. The circumferential position of weld seam 6 is identified by using seam identification algorithms (later described) and provided to control modules 12 and 14. The positioning of probe 2 is controlled by the control modules 12 and 14, so that probe 2 moves to follow seam 6 while the pipe is proceeding.

Figure 4:
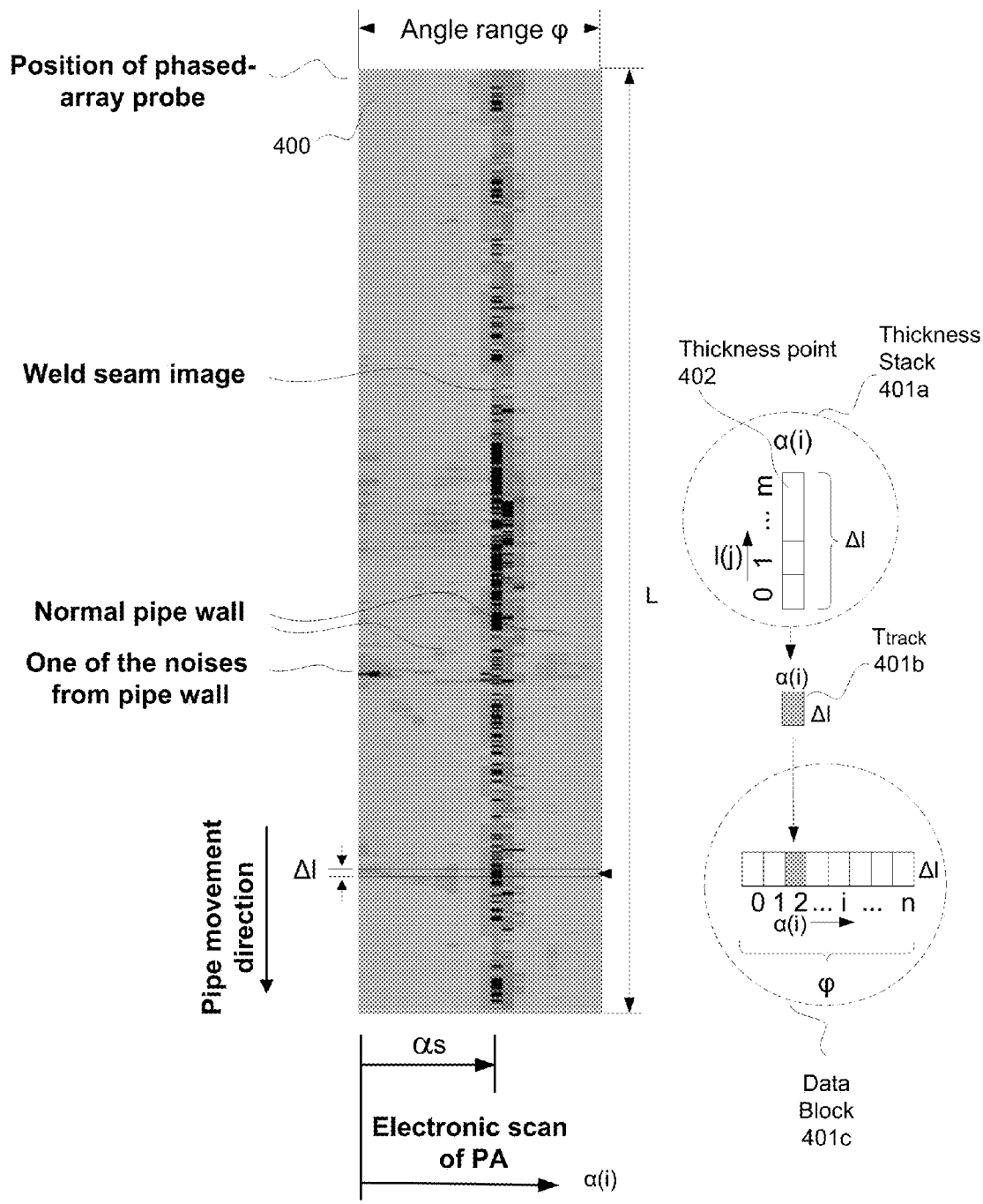
FIG. 4 is a thickness/C-scan image showing the weld seam with obvious thickness variations compare to normal non-welded part of material.

It is preferable that the weld seam tracking system use a data presentation format, such as C-scan, that is normally used by the PA inspection system due to the obvious advantage of consolidating PA scan operations for both seam tracking and inspection purposes. However, it can be appreciated by those skilled in the art that many types of PA scans, such as B-scan, A-scan and S-scan can also provide information for weld seam tracing purposes, provided that the echoes from the weld seam and its vicinity are provided in real time and thickness or other material characteristics of each cell within the geometric grid of the scanned test object can be deduced. Henceforth, the word 'thickness point' will be used to denote the smallest region in a C-scan that can contain a single measurement result, which in some cases may be derived from a plurality of real time measurements. Exemplary thickness point 402 is shown in FIG. 4.

Figure 1A:
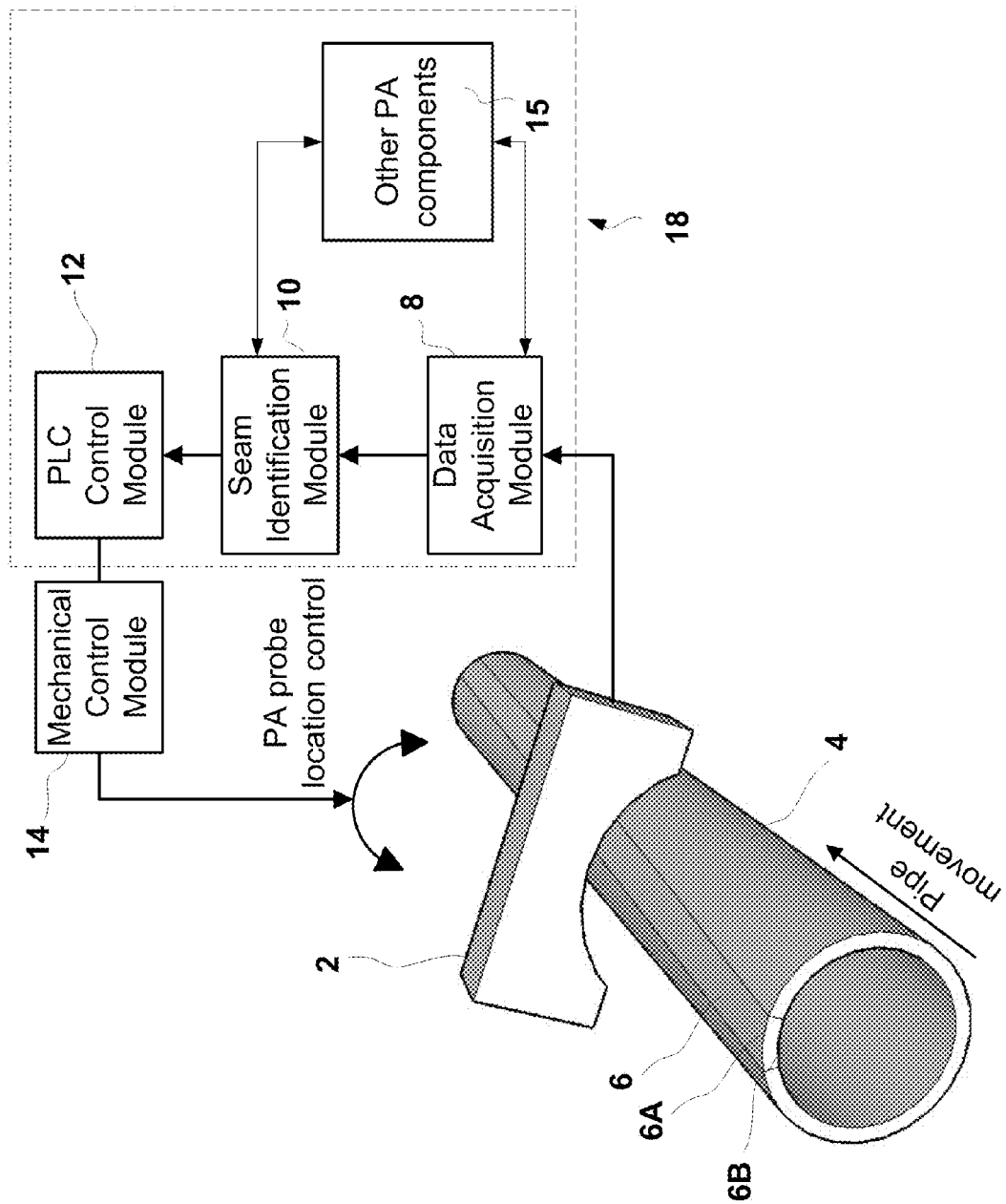
FIG. 1a is a schematic diagram showing a presently disclosed phased array system with weld seam tracking capability.

Alternatively as shown in FIG. 1A, for the obvious advantage of reducing system investment and operational costs, a data acquisition module of a typical PA inspection system can be used, such as the presently designed data acquisition module 8. Similarly, one can modify a processor of an existing design of a PA inspection system to realize the weld seam identification module 10 according to present disclosure. Accordingly, data acquisition module 8, seam identification module 10 and PLC control module 12 and other components of an existing PA system 15 all together form an integral phased array system 18.

Furthermore, existing phased array probe control mechanisms, typically taking input of manual observation and control commands, can be modified to achieve the function of mechanical control module 14 herein described.

It should further be noted that a PA seam tracking and inspection system can be designed to allow both manual and automated PA control and still be within the scope of this disclosure.

In this preferred embodiment, C-scans are used due to their common usage in PA seam inspection. C-scans yielding amplitude, time of flight (TOF) or thickness are three exemplary methods to achieve real-time data for every scanned thickness point 402 of the weld seam and its vicinity.

Detailed description of how to deduce thickness of test object using C-scan generated by PA operations can be found in "*Introduction to Phased-Array Ultrasonic Technology*

*Applications R/D Tech Guideline*", First edition, Library and Archives Canada Cataloging-in-Publication, August 2004, section 4.2.3 C-scan.

Figure 2:
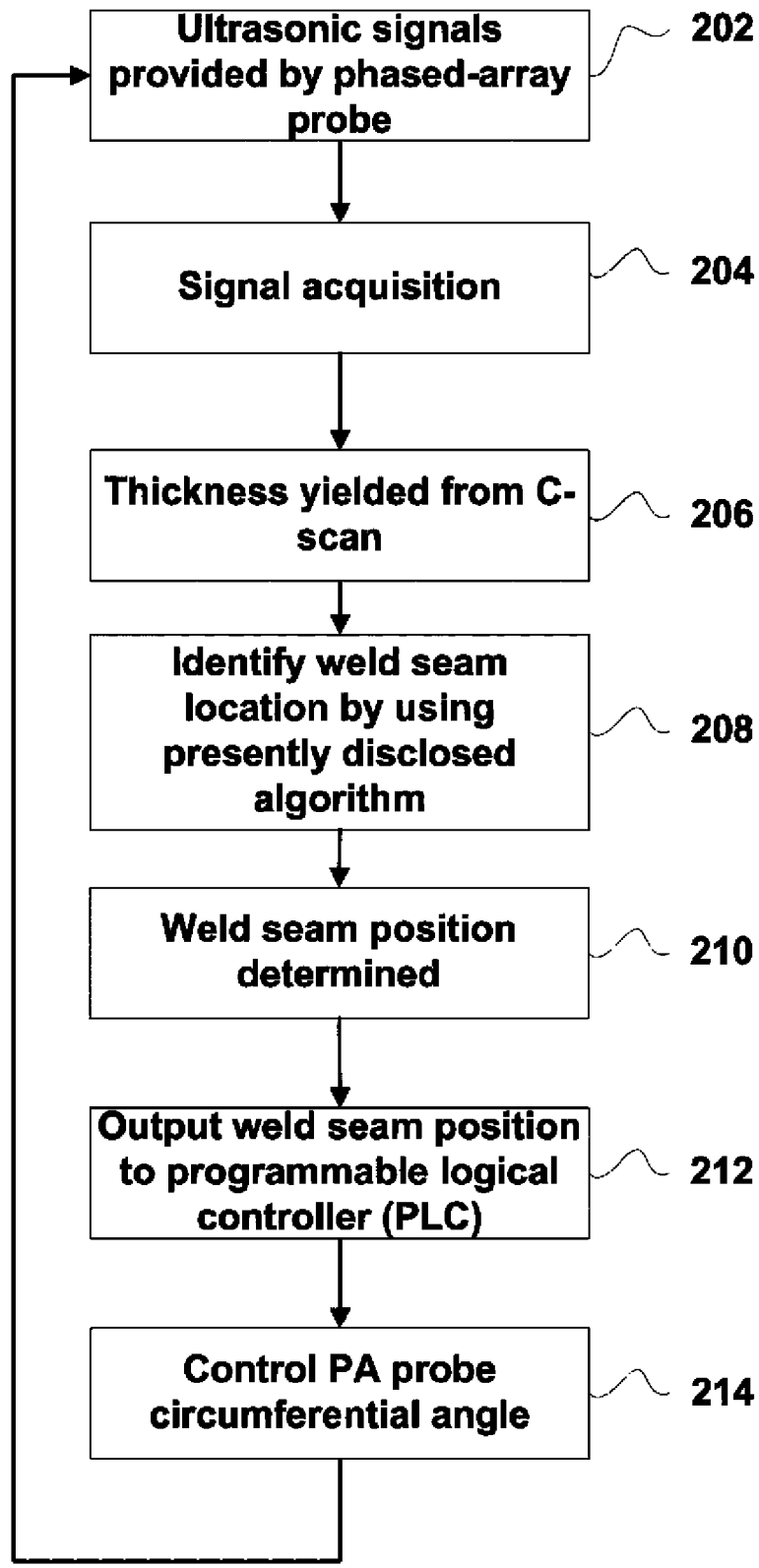
FIG. 2 is a functional block diagram showing the procedure of how a weld seam is tracked using the presently disclosed device.

Reference is now made to FIG. 2, which shows a closed loop of control procedure for the presently disclosed weld seam tracking system. It should be noted that the steps in this control procedure are carried out by data acquisition module 8, weld seam identification module 10 and control modules 12 and 14.

Prior to step 202, weld seam 6 is positioned at a predetermined circumferential location with respect to the sensor surface of PA probe 2, or vice versa. Preferably, the location will be the circumferential center of the linear scan range of PA probe 2 shown as angle $\alpha_S$ in FIG. 3. In step 202, ultrasonic echo signals are provided by a PA probe 2 to acquisition module 8, in which the signals are acquired. In Step 204, the echo signals are preferably processed for both seam tracking and inspection purposes. Then in step 206, a C-scan of the thickness information associated with the test target is generated in a way conventional to a typical PA seam weld inspection system. In step 208, the C-scan thickness information is processed by seam identification module 10 using an algorithm (later described) that tracks the location of the weld seam. While pipe 4 is loaded and subsequently fed through probe 2, the circumferential position of seam 6 determined in step 210 is identified as 'weld seam tracking angle' $\alpha_S$ described later in reference to FIG. 4.

In step 212, the weld seam tracking angle position $\alpha_S$ is provided to a programmable logical controller (PLC), which then mechanically controls the position of the phased-array probe to ensure its alignment with the weld seam 6 in step 214.

Figure 3:
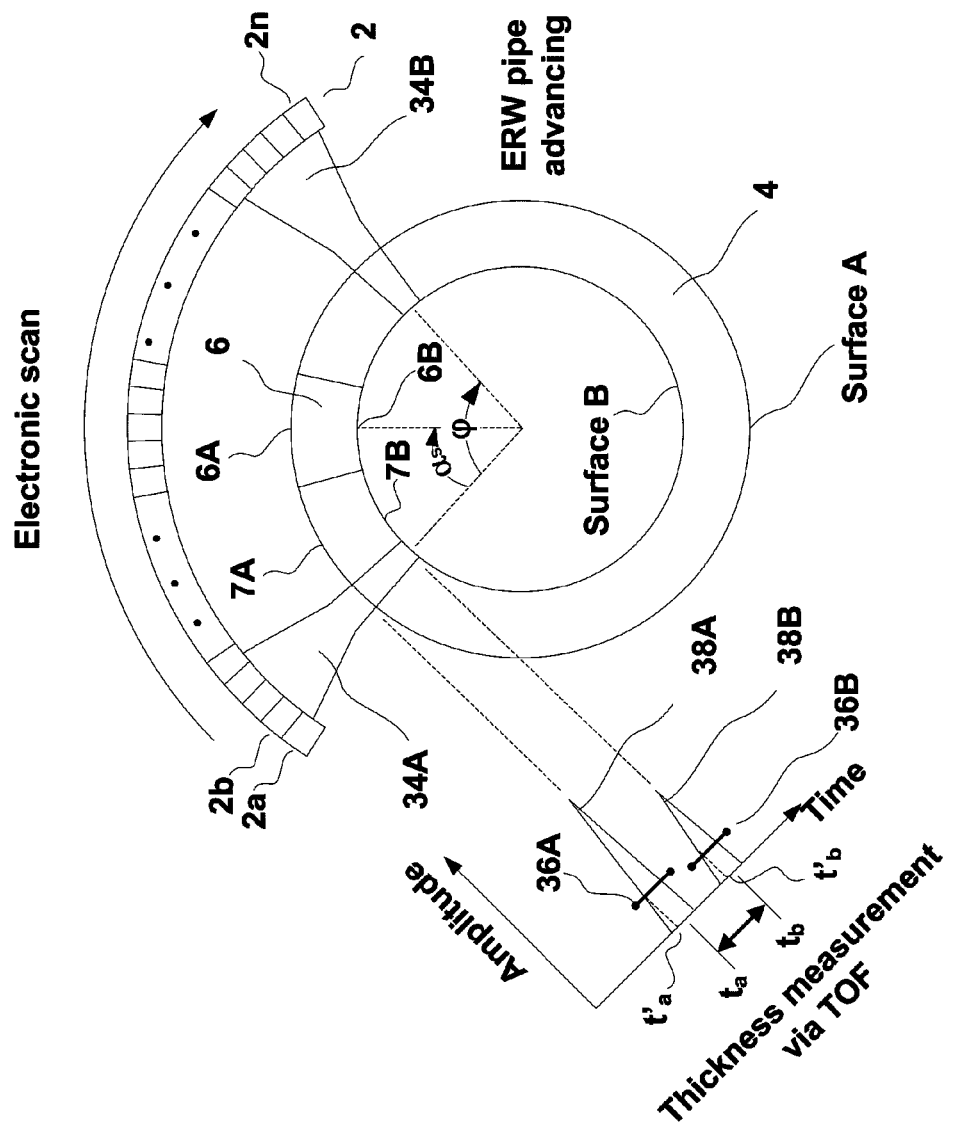
FIG. 3 is a diagram showing how the weld seam is identified by the phased array system by measuring thickness via TOF (Time of Flight).
Figure 5:
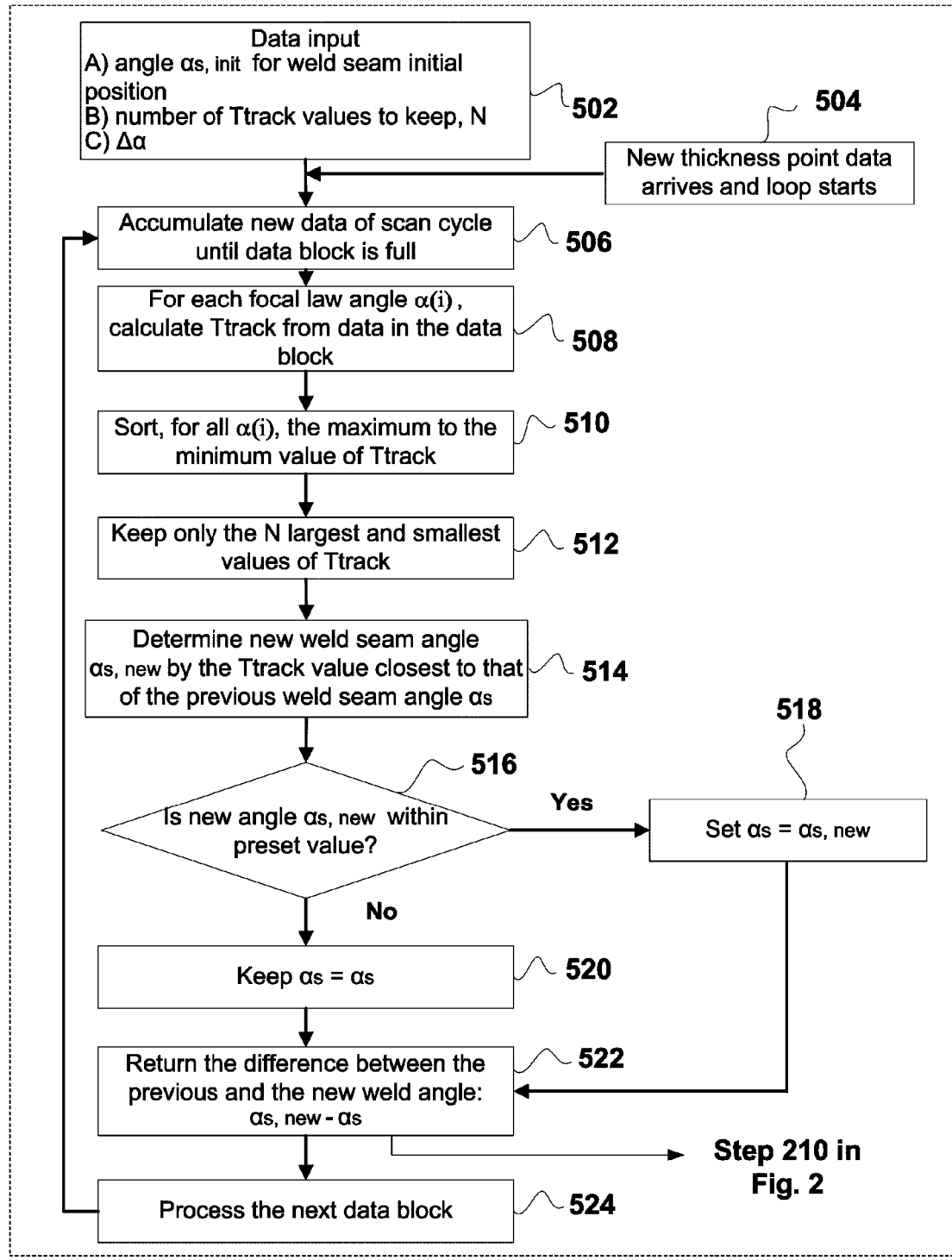
FIG. 5 is a flow chart showing the algorithm used to identify and track the weld seam.
Figure 7:
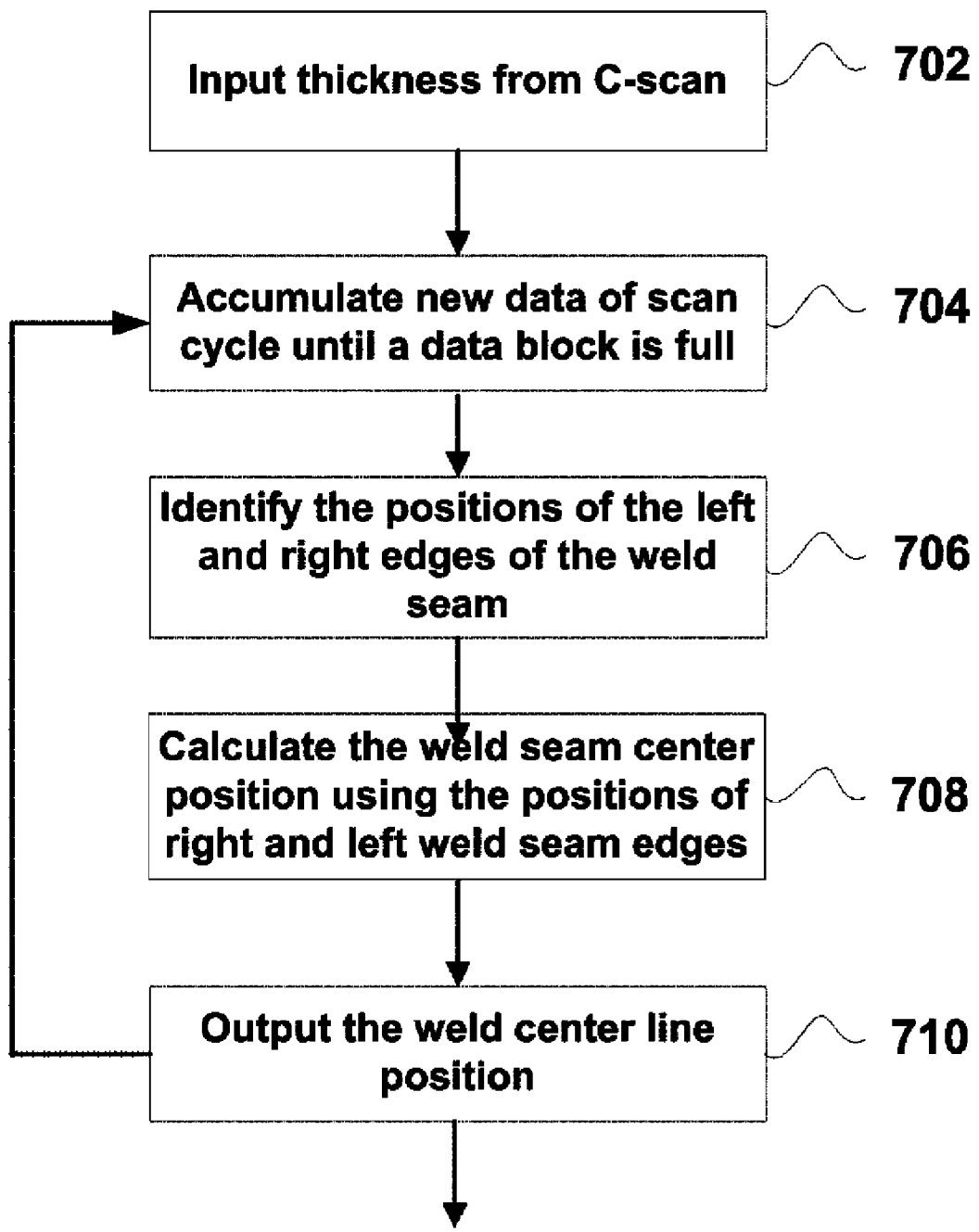
FIG. 7 is a flow chart showing the algorithm used to identify and track the center of the weld seam.
Figure 9:
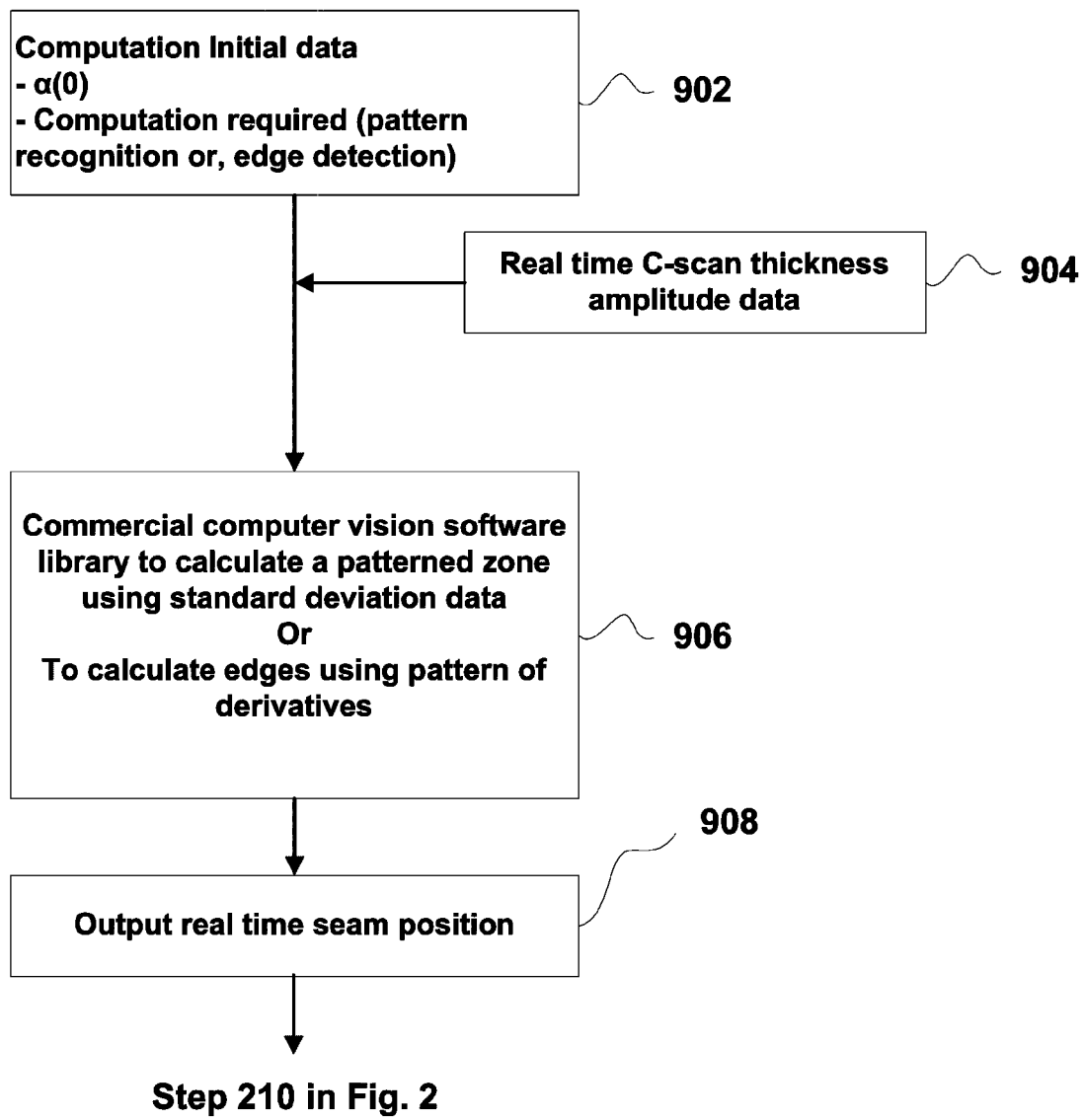
FIG. 9 is a flow chart diagram showing an alternative algorithm whereas a commercial computer software library is used to identify the weld seam.

The geometric aspects used to obtain the thickness at a weld seam and its vicinity are described in FIG. 3 and the algorithm to determine the weld seam location using these aspects is described in FIGS. 5, 7 and 9. It should be noted for FIG. 3 that the exterior and interior surfaces of pipe 4 are referred to as 'surface A' and 'surface B', respectively. Connecting surface 6A is part of surface A and connecting surface 6B is part of surface B.

As shown in FIG. 3, phased array probe 2, electronically controlled by acquisition module 8, performs linear scans by transmitting and receiving multiple sound beams to cover the weld seam and its vicinity according a predetermined set of focal laws. The focal laws applied by acquisition module 8 (FIGS. 1 and 1a) determine the beam incidence angle, the number of elements to use for each aperture, the step of elements of the electronic linear scan, and the focus position within the pipe wall. As a result, the whole seam region within angle φ is scanned while the pipe is welded, trimmed, and passed under probe 2. One can refer to *Introduction to Phased—Array Ultrasonic Technology Applications R/D Tech Guideline*", First edition, Library and Archives Canada Cataloging-in-Publication, August 2004, sec. 1.2, for detailed information about phased array operation and focal laws.

For each step of pipe's axial movement, the system performs at least one complete linear scan cycle by transmitting/receiving from the fired first focal law 34A to the last fired focal law 34B. The timing of the linear scan cycle is synchronized with the pipe's axial movement. For example, for each 1 mm of axial movement of the welded pipe, a cycle of linear scan covering the weld seam and its vicinity is executed. In this way, the electronic linear scan covers the weld seam and its vicinity represented by the angle φ for the whole pipe length. It should be noted that it is also within the scope of the present disclosure to apply the linear scan measurement when the pipe is momentarily at rest between discrete axial movements.

Continuing with FIG. 3, in the coordinates in the left-lower half of the figure, two waveforms are shown in a time-amplitude coordinates, with waveform 38A representing the echo signal reflected from the outer surface 6A and waveform 38B representing the echo signal reflected from the inner surface 6B. The measurement of thickness between 6A and 6B can be deduced by the time difference between the two peaks of the waveforms as:

$$\text{Thickness} = \frac{t_b - t_a}{2v}, \quad [\text{Eq. 1}]$$

where $t_a$ and $t_b$ are the TOFs measured respectively at the two peaks of the echoes from the inner and outer connecting surfaces 6A and 6B, respectively, and v is the constant velocity of the echoes traveling in the pipe material. The TOFs are divided by 2 to account for the echo travel time to and from the back wall.

Similarly, the thickness of the non-welded vicinity can also be determined by the echo TOF between exterior pipe wall 7A and interior pipe wall 7B. The thickness of the non-welded vicinity may also be provided as a pre-determined value to the weld seam tracking system. The differences between the welded and non-welded regions along the pipe axial direction, which is often subtle, are then analyzed by the seam tracking algorithms later described.

It should be noted that the thickness measurement does not have to be performed using echo peaks. Indeed, any reference point in a common respective location on each of the two echoes may be used to determine the thickness. For example, the TOFs used for thickness measurement can also be the times $t'_a$ and $t'_b$ defined as the times when the signal amplitudes break time gates 36A and 36B as shown in FIG. 3. (see Eq. 2).

$$\text{Thickness} = \frac{t'_b - t'_a}{2v}. \quad [\text{Eq. 2}]$$

The above thickness measurement is repeated for all sound beams that cover the weld seam and its vicinity for the whole length of pipe 4.

Next, the thicknesses of the weld seam and its vicinity are recorded to form thickness points 402 within the two-dimensional C-scan 400, as shown in FIG. 4.

In this exemplary embodiment, C-scan 400 shown in FIG. 4 is a two-dimensional image, with the x direction representing the weld pipe circumferential scan range of angle φ and the y direction representing the axial movement direction of pipe 4 and length L of the C-scan region. C-scan 400 is comprised of all thickness point 402 values acquired across circumferential angle φ over length L. The weld seam appears on C-scan 400 as a set of thickness points with contrasting shade (or color) depicting different thickness values as compared to the thickness values for the non-welded vicinity. Henceforth, a plurality of thickness points 402 will be referred to as 'thickness points'.

It is important to note that there are many methods to render thickness values that can be used for C-scan 400, or other data representations, that are well known to those skilled in the art. The present disclosure describes exemplary methods and is not limited in this regard.

In some cases the contrast between thickness points is clearly evident and in other cases it is not. The contrast between the weld seam and the non-welded pipe wall vicinity can be low due to minor differences in thickness, noise, flaw detection, or other measurement anomalies. Regardless of the degree of contrast between thickness points, the thickness data is provided to weld seam identification module 10, in order to calculate the angle position $\alpha_S$ of the weld seam line for tracking by probe 2.

It is worth noting for the preferred embodiment that the C-scan image showing the weld seam location is not typically used for manual guidance of probe 2. The C-scan information identifying the real-time weld seam location is rather processed and fed to control modules 12 and 14 to adjust the position of probe 2 to follow the weld seam automatically. Nevertheless, the probe position can be manually adjusted by the operator based on his/her reading of the C-scan 400 information.

Referring now to FIG. 5, a flowchart is shown that illustrates an exemplary algorithm for weld seam identification module 10 (FIGS. 1 and 1a) to identify real-time weld seam locations. This flowchart is also an elaboration of step 208 in FIG. 2.

According to FIG. 5, the algorithm comprises mainly two functional portions, a data-feeding portion (step 502 and step 504) and a loop that processes the input thickness provided by the C-scan. The latter is performed on successive sections of the welded part in the axial direction to locate the new weld seam line position $\alpha_S$ (steps 506-522). Before the algorithm is carried out, phased-array probe 2 is centered along weld seam 6 which also centers the weld seam on the C-scan as shown in FIGS. 3 and 4. Exemplary angle $\alpha_S$ in FIG. 4, corresponds to the circumferential location of the largest thickness difference compared to the non-welded vicinity. This location is known as the weld seam tracking point. The initial tracking point, $\alpha_{S,init}$, is provided and stored by the operator or some other means to indicate the reference $\alpha_S$, angle. It should be noted that after weld trimming the weld seam will be convex or concave—i.e. thicker or thinner than the material of the non-welded vicinity, respectively.

In the initial step 504, the measured or otherwise known thickness of the seam is stored for subsequent use. In step 502, the initially identified $\alpha$ value associated with the thickness entered in step 504 is saved in internal memory as $\alpha_{S, init}$. After step 502, the production line is enabled to start when invoked by step 504 and pipe 4 starts moving in an axial direction. After new data for thickness point 402 arrives at step 504, the loop begins with step 506. At the first step of the loop, step 506, real-time thickness C-scan data is accumulated as the weld seam and its vicinity is scanned across the full linear scan range of angle $\phi$ at each $\alpha(i)$ (i.e. $\alpha(0)$, $\alpha(1)$, ..., $\alpha(n)$) while pipe 4 moves a distance $\Delta 1$ in its axial direction. Step 506 continues until the data block (401c in FIG. 4) is full. The size of the data block is determined by the number of acquisitions that occur while the pipe moves a distance $\Delta 1$.

It is worth noting that the initial tracking point $\alpha_{S, init}$ can be set to any circumferential position on the seam, but is preferably located at either the nadir, or apex of the weld seam.

As shown in FIG. 4, data block 401c is comprised of data stacks 401a, each of which is associated with a given focal law angle $\alpha(i)$ and is comprised of m thickness points 402 over the axial length of $\Delta 1$ (i.e. 1(0), 1(1), ... 1(m)).

Continuing with FIGS. 4 and 5, at step 508, data stack 401a is reduced to one value $T_{Track}$ which is equivalent to the sum, average or other representation of its thickness point 402 values across $\Delta 1$ for each focal law angle $\alpha(i)$. This step suppresses noise and echoes reflected from true flaws in the weld seam or in its vicinity. It should be noted that for conventional welding system applications, the position of the weld seam wanders very slowly along the pipe. For example, it is not uncommon for the weld seam position to wander in the order of a few degrees per 50 m, whereas the data block length is typically in the order of tens of millimeters and the angular resolution of the C-scan is in order of one degree. Accordingly, the reduction of data stack 401a values to one representative value, $T_{Track}$ 401b, as described above for step 508, reduces the system's susceptibility to noise and thereby enhances the contrast of the thickness variation.

In step 510, the $T_{Track}$ values are sorted and stored with their associated focal law angle $\alpha(i)$. In step 512 the N largest and N smallest cell $T_{Track}$ values are each stored with their associated focal law angle $\alpha(i)$. The number of values N, to store can be predetermined by the operator, e.g. 3. It should be noted for step 512 that, although not shown, $T_{Track}$ values used for tracking purposes may be only the N largest values if the contour of weld seam 6 is known to be always thicker than the non-welded region. If the contour of weld seam 6 is known to be always thinner than the non-welded region, the N smallest values may be used. Alternatively, the N largest absolute values of the difference between the $T_{Track}$ value of the welded and non-welded region may be used if the relative thickness between the weld contour and non-welded region is known or not.

In step 514, the stored value closest to the value associated with the previous known weld seam angle $\alpha_S$ (the first of which is the initial weld seam angle, $\alpha_{S, init}$, determined by the operator in step 502) provides the new angle of weld seam, $\alpha_{S, new}$. The difference between the previous angle $\alpha_S$ and $\alpha_{S,new}$ is compared in step 516. In step 520, if the angle difference is not within a preset value $\Delta\alpha$, meaning the seam wanders unrealistically, the angle of the previous cycle, $\alpha_S$ is kept. If the difference is within $\Delta\alpha$, the new angle $\alpha_{S, new}$ is stored as $\alpha_S$ in step 518. The pre-determined $\Delta\alpha$ depends on a few, factors, including the size of the welded sheet, the diameter of the welded pipe, and the focal law applied. A $\Delta\alpha$ value corresponding to 3-4 focal law positions, $\alpha(i)$, is preferably set for the present disclosure.

It should be noted that although not shown in FIG. 5, thickness acceptance criteria may also be applied to thickness points 402 and $T_{Track}$ 401b to filter out value anomalies caused by noise, sensor contact discontinuity, or other events. This is possible due to the fact that thickness tolerances of the welded and non-welded region are known before the weld inspection and seam tracking system is employed.

The new angle, $\alpha_{S, new}$, is then compared to the previous $\alpha_S$. In step 522 the difference between $\alpha_{S, new}$ and $\alpha_S$ is provided to control modules 12 and 14 (step 212 in FIG. 2) the function of which is to cancel the difference by re-aligning probe 2's center or other predetermined element's circumferential position at an angle $\alpha_S$, new. The weld seam tracking for current loop ends at step 524 and the program goes back to step 506 to continue to the next loop.

It should be noted that the algorithm described above in association with FIG. 5 may be adapted to identify any point of interest within the weld seam that has a $T_{Track}$ thickness value closest to the previous value identified for weld seam angle $\alpha_S$. That is to say, the identified point could be any point within the weld seam and need not be the apex or nadir. For the sake of identification, this algorithm is herein called 'Any Point on Seam' algorithm.

Figure 6:
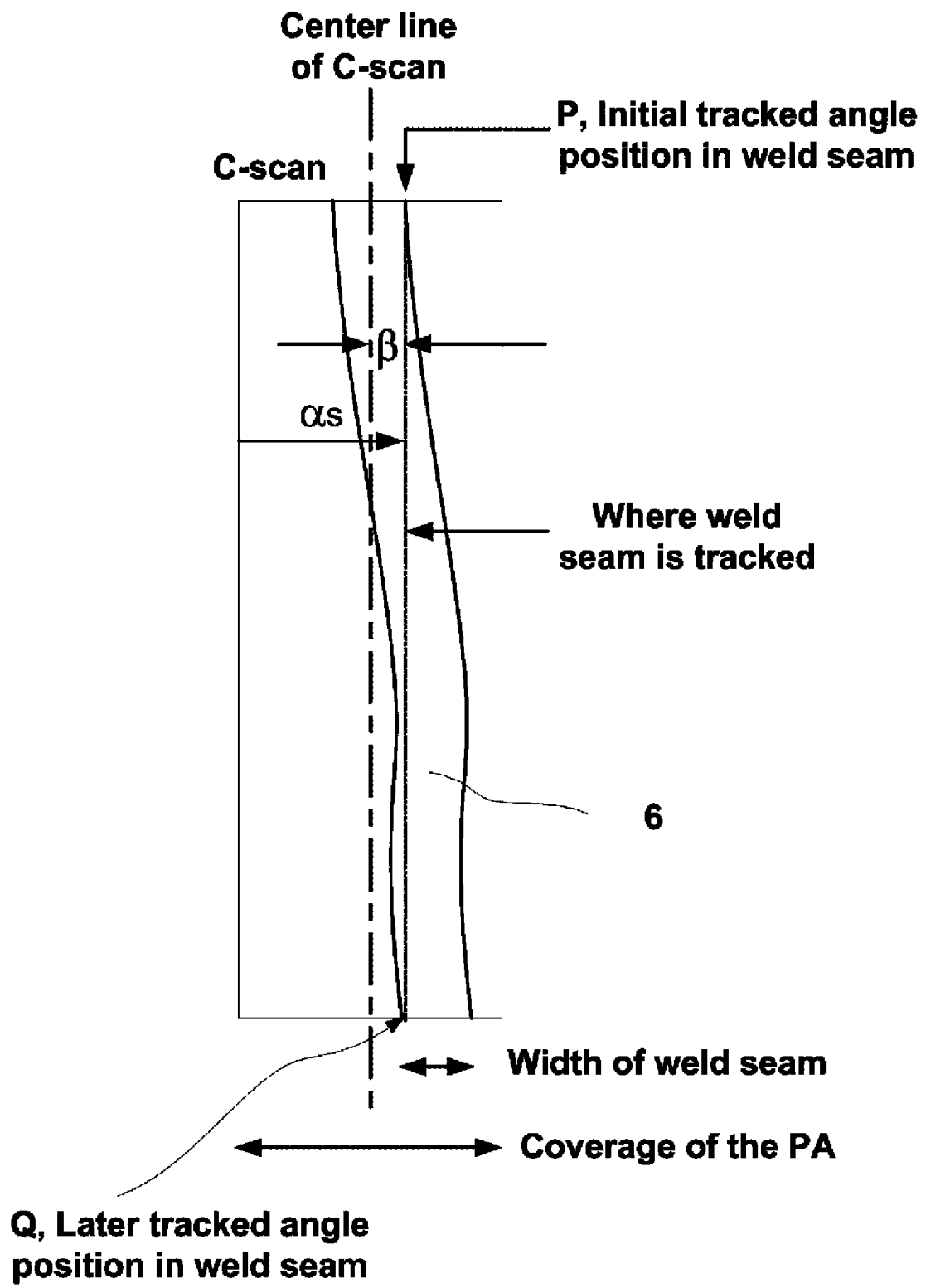
FIG. 6 is a diagram showing the relationship of the width of a weld seam and the scan coverage of a PA probe, when any spot largest thickness variation is identified as the seam location.

FIG. 6 presents the relationship of the width of a weld seam and the scan coverage of a PA probe, when 'Any Point on Seam' is used to identify the seam location using the above described algorithm.

As shown in FIG. 6, the weld seam 6 is initially centered in the C-scan by the operator. Because the angle $\alpha_S$ as tracked using the above 'Any Point on Seam' algorithm, it can be located at any position within the width of seam 6. As a result, the tracked angle position can drift, in one extreme exemplary case as shown here, from one edge of the seam at point P to the other edge of the seam at point Q constituting weld seam tracking line PQ. This is due to a substantially equivalent $T_{Track}$ value measured along weld seam tracking line PQ.

Also note in FIG. 6 that probe 2 can be positioned at an angle $\alpha_S$ with an offset to its center element. That is to say, it is acceptable to have an angle offset $\beta$ between the center of probe 2 and the element that is set to weld seam angle $\alpha_S$.

Care needs to be taken when using the above described 'Any Point on Seam' tracking algorithm. Specifically, in order to avoid any loss of tracking, the coverage of the PA probe 2 should preferably be at least three times of the width of the weld seam, whereas angle shift $\beta$ should be less than half of the initially identified width of the weld seam.

As shown in FIG. 7, an alternative to the 'Any Point on Seam' algorithm may be used referred to herein as the 'Approximate Center of the Seam' algorithm which, as the name implies, identifies and tracks the approximate center line of the seam. Similar to what was used in 'Any Point on Seam' algorithm, in step 702, for each length of data block 401c, thickness data for all measurement cells covered in the block is inputted to the seam identification algorithm 208. In step 704, for each specific focal law angle $\alpha(i)$, all values of each thickness point from C-scan in each thickness stack of the data block are summed, averaged, or otherwise represented. It should be noted that steps 702 and 704 can be the same or very similar to steps 502, 506 and 508 as shown in FIG. 5. In step 706, the left and right edges of the weld seam are identified. In step 708, the weld seam center is found by determining the geometric center between the left and right edges. In step 710, the seam center position is provided to the control modules 12 and 14, in one case, to align the center of probe 2 with the identified seam center.

There are many ways to locate the left and right edges of the seam using the 'Approximate Center of the Seam' algorithm. Preferably this is accomplished by identifying the demarcation of the weld seam edges with respect to the non-welded vicinity. For example, left and right edges can be correlated to $T_{Track}$ values indicating the sudden on-set of a weld region compared to $T_{Track}$ values of non-welded region of the part. The approximate center point for this respective data block is therefore found after the left and right edges are determined.

It is worth noting that in order to find either any one point in the weld seam or the center of the weld seam, many other calculation methods can be used within the scope of present disclosure.

Figure 8:
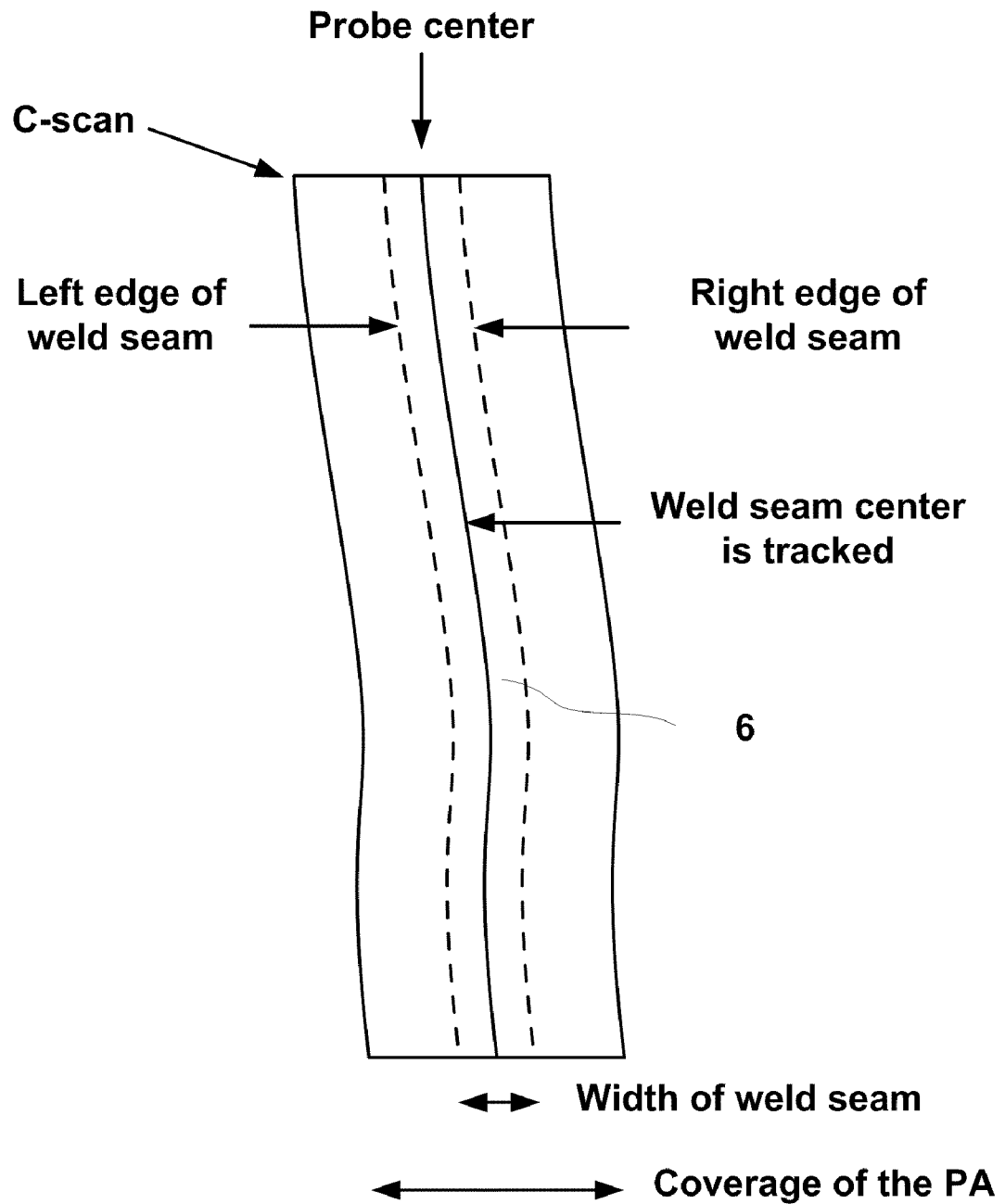
FIG. 8 is a diagram showing the relationship of the width of a weld seam and the scan coverage of a PA probe, when center of the thickness variation is identified as the seam location.

FIG. 8 is a diagram showing a simulated result when the approximate center of the seam is tracked by the center element of probe 2.

Although the 'Approximate Center of the Seam' tracking algorithm may more accurately find the center of a weld seam line once the location of the left and right seam boundaries are identified, it does have a limitation compared to the 'Any Spot on the Seam' tracking algorithm. Specifically, when the circumferential weld seam drift exceeds the linear scan range angle $\phi$, probe 2 must be mechanically repositioned over the weld line sooner, and more often, than it would have to be for the 'Any Spot on the Seam' tracking algorithm. The need for probe movement impacts the efficiency of the weld seam scanning process as compared to a stationary probe performing an electronic linear scan. The reason for this is that for the 'Approximate Center of the Seam' algorithm, both the left and right weld seam boundary points must be scanned instead of just the one narrow weld seam point. Accordingly, the 'Any Spot on the Seam' algorithm will tolerate a greater degree of weld seam drift before the location of probe 2 needs to be adjusted.

It is worth noting that, for all embodiments of the present disclosure, to avoid disruptive or excessive angular (circumferential) repositioning of the PA probe 2, such adjustments are preferably limited to instances where the angular (circumferential) positions of the seam has drifted by more than a predetermined amount.

Further alternatively, commercially available computer vision software programs can be used to process PA thickness data, such as C-scan data. As an example, software package Hough Lines of Open CV offered by Intel Library can be used for this purpose. Within the software package, pattern recognition functions can be used to detect outstanding standard deviation of C-scan data. Edge detection functions may also be used to detect outstanding derivatives of C-scan data. Certain modification of such software libraries might be needed to make them fit for weld seam tracking purpose.

FIG. 9 is a schematic functional flow chart showing an exemplary use of commercial computer vision software. At step 902, while welding production is yet to be started, initial seam position and computation requirement parameters are provided as the input of the program. Then right after the welding production is started, at step 904, real time C-scan thickness or amplitude data is provided from the PA system. Then at step 906, the commercial computer vision software or customized library computes the standard deviation of the thickness data for each focal law beam and finds a pattern of zone presenting the highest, e.g., 20% of standard deviation. Alternatively at step 906, the software can find an edge characterized by a pattern of derivatives that could indicate a substantially continuous axial line. At step 908, the software outputs to the control modules 12 and 14 with the identified track of the weld seam for the position of PA probe 2 to be changed if required.

It's also worth noting that, the above described approach is preferably achieved by making use of a thickness or flaw inspection PA probe for both seam tracking and inspection purposes.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. An ultrasonic inspection system, comprising:
   a phased array probe suitable for inspecting a test object having a weld seam along the longitudinal direction of the test object, wherein the inspection system comprises a seam identifier module configured to obtain data from the probe, to determine the location of the seam and to position the probe to track the seam when the test object is being passed under a test zone of the probe;
   wherein the location of the weld seam is determined by identifying geometric properties of the weld seam, which are identified by analyzing ultrasonic echo signals reflected by a first test object surface and a second test object surface; and, the first test object surface is a single continuous surface having a first connecting surface of the seam and the second test object surface is a single continuous surface having a second connecting surface of the seam.

2. The system of claim 1, wherein the geometric properties comprise the thickness of the seam compared to thickness measurements obtained at non-welded parts of the test object.

3. The system of claim 1, wherein the geometric properties are identified by analyzing times of flight of echo signals reflected by the first and second surfaces.

4. The system of claim 1, in which the position of the geometric properties are calculated by analyzing continuous C-SCAN data to obtain thickness information of the test object for each measurement cell in a test zone.

5. The system of claim 1, in which the seam is identified by any spot within the seam in one unit length of the seam.

6. The system of claim 1, in which the seam is identified by spots located substantially close to the center points of the width of the seam.

7. The system of claim 1 further comprising,
an ultrasonic signal acquisition module configured to receive ultrasonic echo signal from the test object;
a weld seam identification unit working with the seam identifier module to analyze the signal and identify geometric properties of the seam and to compare said properties to the non-welded part of the test object and to identify locations of the seam;
a controller configured to issue positioning commands to position the probe according to the location of the seam; and
a mechanical adjustment unit responsive to the controller and configured to adjust the probe location according to the positioning commands.

8. The system of claim 7, wherein the geometric properties are in the thickness of the seam which are compared to geometric properties of non-welded parts of the test object.

9. The system of claim 7, wherein the geometric properties are identified by analyzing times of flight in the echo signals reflected by the first and the second surfaces.

10. The system of claim 7, in which the position of the geometric properties are continuously calculated by analyzing continuous C-SCAN data to obtain thickness information of the test object for each data block in the test zone.

11. A weld seam tracking apparatus operable with an ultrasonic phased array inspection system having a phased array probe suitable for inspecting a test object having a weld seam along the longitudinal direction of the test object, wherein the probe receives ultrasonic echo signal from the test object, and wherein the seam tracking apparatus comprises an ultrasonic signal acquisition module receiving data processed by the inspection system, the apparatus comprising:
a weld seam identification unit configured to analyze the data and to identify the location of the seam by analyzing geometric properties of the seam compared to non-seamed parts of the test object and to further identify locations of the seam;
a programmable logical controller configured to issue positioning commands to position the probe according to the locations of the seam;
a probe mechanical adjustment unit configured to adjust the probe location according to the positioning commands;
wherein the geometric properties of the weld seam are identified by analyzing ultrasonic echo signals reflected by a first test object surface and a second test object surface; and,
the first test object surface is a single continuous surface having a first connecting surface of the seam and the second test object surface is a single continuous surface having a second connecting surface of the seam.

12. The apparatus of claim 11, wherein the geometric properties are in the thickness of the seam and are compared to geometric properties of non-seamed parts of the test object.

13. The apparatus of claim 11, wherein the geometric properties are identified by analyzing times of flight of echo signals reflected by the first and second surfaces.

14. The apparatus of claim 11, in which the position of the geometric properties are continuously calculated by analyzing continuous C-SCAN data yielding thickness information of the test object for each measurement cell in the test zone.

15. A method for tracking a welded seam on a test object, the method comprising the steps of:
positioning a phased array probe across the welded seam, at an initial longitudinal location thereon;
moving the test object in its longitudinal direction relative to the phased array probe;
firing the probe and receiving echo signals from the test object;
providing test data indicating position of the weld seam;
concurrently to the step of moving the test object, adjusting the position of a phased array probe by following the position of welded seam;
wherein the position of the weld seam is determined by identifying geometric properties of the weld seam, which are identified by analyzing ultrasonic echo signals reflected by a first test object surface and a second test object surface; and,
the first test object surface is a single continuous surface having a first connecting surface of the seam and the second test object surface is a single continuous surface having a second connecting surface of the seam.

16. The method of claim 15, wherein the phased array probe utilizes ultrasonic pulses to produce C-scan data.

17. The method of claim 16, wherein the obtained C-scan data is utilized both for positioning the phased array probe relative to the welded seam and to obtain and develop data indicative of the structural integrity of the welded seam.

* * * * *